United States Patent [19]

Koizumi et al.

[11] 4,377,342
[45] Mar. 22, 1983

[54] ZEEMAN ATOMIC ABSORPTION SPECTROPHOTOMETER

[75] Inventors: Hideaki Koizumi, Tokyo; Hitoshi Sawakabu, Katsuta, both of Japan

[73] Assignees: Hitachi, Ltd.; Hitachi Naka Seiki Kabushiki Kaisha, both of Tokyo, Japan

[21] Appl. No.: 236,995

[22] Filed: Feb. 23, 1981

[30] Foreign Application Priority Data

Feb. 22, 1980 [JP] Japan .................................. 55-20439

[51] Int. Cl.³ .......................... G01J 3/42; G01N 21/74
[52] U.S. Cl. .................................. 356/307; 356/312; 364/498
[58] Field of Search ........................ 356/307, 312, 315; 364/498

[56] References Cited

U.S. PATENT DOCUMENTS 4,035,083 7/1977 Woodriff et al. ............... 356/307 X

FOREIGN PATENT DOCUMENTS 474204 6/1973 Australia ............................. 356/307

OTHER PUBLICATIONS

Koizumi et al., Spectrachimica Acta, vol. 31 B, No. 10-12, 1976, pp. 523-535.

Primary Examiner—F. L. Evans
Attorney, Agent, or Firm—Antonelli, Terry & Wands

[57] ABSTRACT

In a Zeeman atomic absorption spectrophotometer, an atomic absorption signal in an atomization stage is observed. The length of time between an instant at which the signal initially attains a predetermined absorbance and an instant at which the signal attains the same predetermined absorbance for the last time during the atomization stage is measured. By utilizing this time measurement as an indication of concentration, the concentration of the sample can be measured at higher concentrations than the limit concentration in the analysis by a conventional apparatus of this kind.

40 Claims, 9 Drawing Figures

4,377,342

ZEEMAN ATOMIC ABSORPTION SPECTROPHOTOMETER

BACKGROUND OF THE INVENTION

The present invention relates to a Zeeman atomic absorption spectrophotometer.

An atomic absorption spectrophotometer is known as an apparatus for use in quantitatively analyzing metal elements contained in sewage, food, urine or the like. Among the atomic absorption spectrophotometers, one using the Zeeman effect is known as an apparatus which permits the analyzing of a very small quantity of metal and which has a high sensitivity. By the use of the Zeeman effect, the detecting limit is improved to a higher level by one or two orders of magnitude than that of an ordinary prior art atomic absorption spectrophotometer. Zeeman atomic absorption spectrophotometry has recently been studied by many scientists and has been observed to be a highly reliable and promising technique.

Still there is a major problem in that Zeeman atomic absorption spectrophotometry has a draw-back phenomenon in its calibration curve. This draw-back phenomenon will be explained with reference to FIG. 1.

FIG. 1 shows an example of the calibration curve of cadmium, which is measured by the use of the conventional Zeeman atomic absorption spectrophotometer, as described in H. Koizumi et al, Analytical Chemistry, Vol. 49, No. 8, p. 1106 (1977). This spectrophotometer is so constructed that a magnetic field intersecting an optical axis at a right angle is impressed upon a sample atomizing unit and that a rotating polarizing element is interposed between a light source and the sample atomizing unit. This produces a pair of polarized light components which are, respectively, perpendicular to and parallel to the magnetic field. The parallel component is absorbed by the vaporized sample but the perpendicular component is not. Thus, the difference in absorption between the two components gives a measurement of the absorption of the sample with a correction for background absorption. A calibration curve for the material being analyzed is drawn by the use of the peak value of the difference between the beams having the polarized components which have passed through the polarizing element and which intersect each other at a right angle.

As is apparent from FIG. 1, the difference absorption is gradually increased with the increase in concentration. As is also apparent from FIG. 1, the curvature of the calibration curve becomes higher as the concentration increases. Moreover, the calibration curve has a peak in the vicinity of 40 ppb and exhibits a dropping phenomenon in the higher concentration range. This dropping phenomenon is the draw-back phenomenon of the calibration curve.

Since the calibration curve becomes a two-valued function in the high concentration range because of the draw-back phenomenon, it is impossible to accomplish the measurement. In the example shown in FIG. 1, moreover, the curvature of the calibration curve is greater than 25 ppb, for example, so that sufficient accuracy cannot be attained in the actual analysis.

SUMMARY OF THE INVENTION

It is therefore an object of the present invention to provide a Zeeman atomic absorption spectrophotometer which permits the analyzing of a sample having a higher concentration.

It is another object of the present invention to provide a Zeeman atomic absorption spectrophotometer which can measure a sample having a high concentration more accurately.

According to a feature of the present invention, the length of time during an atomizing stage between the instant at which the intensity of an atomic absorption signal after the compensation of the background absorption with the use of the Zeeman splitting first reaches a preset value and the instant at which the intensity of the atomic absorption signal last reaches the preset value is measured while observing the atomic absorption signal.

DETAILED DESCRIPTION OF THE PREFERRED EMBODIMENT

The draw-back phenomenon can be theoretically explained, as follows. Specifically, in the Zeeman atomic absorption analysis of the type in which a magnetic field is impressed upon a sample atomizing unit, for light coming from the light source and having a component intersecting at a right angle the Zeeman splitting component used to compensate the background absorption, there is obtained a difference signal between the light and the light coming from the light source of the same polarizing plane as such a component as is free from the Zeeman splitting. Here, the absorption due to the atomic absorption is gradually saturated in the high concentration range, whereas the background absorption is linearly increased. As a result, the difference signal is saturated, and the curvature element of the calibration curve, which is intrinsically caused by the atomic absorption, is added, to thereby create the draw-back phenomenon of the calibration curve.

Figure 1:
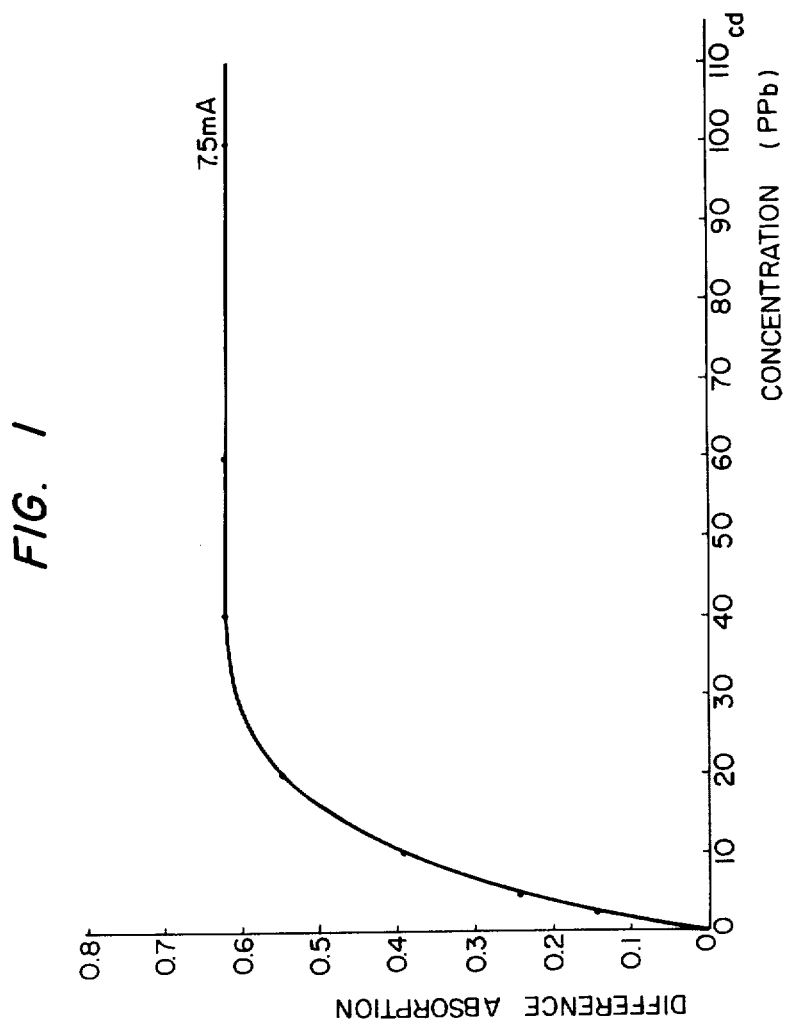
FIG. 1 is an explanatory view of the draw-back phenomenon found in the calibration curve according to the prior art.
Figure 2:
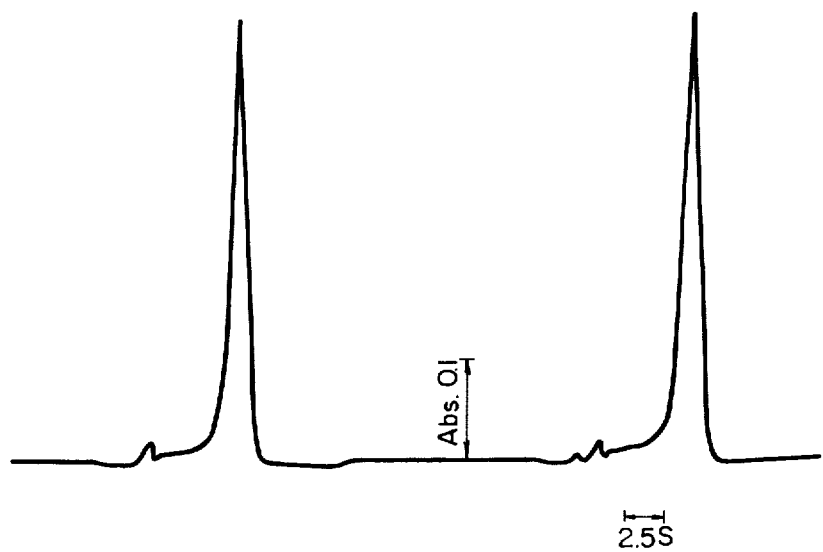
FIG. 2 is a data chart of the difference absorption peak of a sample having a low concentration.

On the other hand, the peak signal of the difference absorption in the low concentration range has a remarkably simple absorption peak as shown in FIG. 2 The example shown in FIG. 2 is that in which measurements were carried out twice for a sample of lead of 200 ppb and 10 $\mu$L. The calibration curve of lead has a smaller curvature up to a relatively high concentration than that of cadmium shown in FIG. 1. According to experiments, however, two-split peaks appear in the range of concentration of higher than 1000 ppb (or 1 ppm), which are different from the absorption peak in FIG. 2.

As a result, the relationship between the absorption peak value and the concentration is complicated.

First of all, the principles underlying the present invention will be explained.

Figure 3:
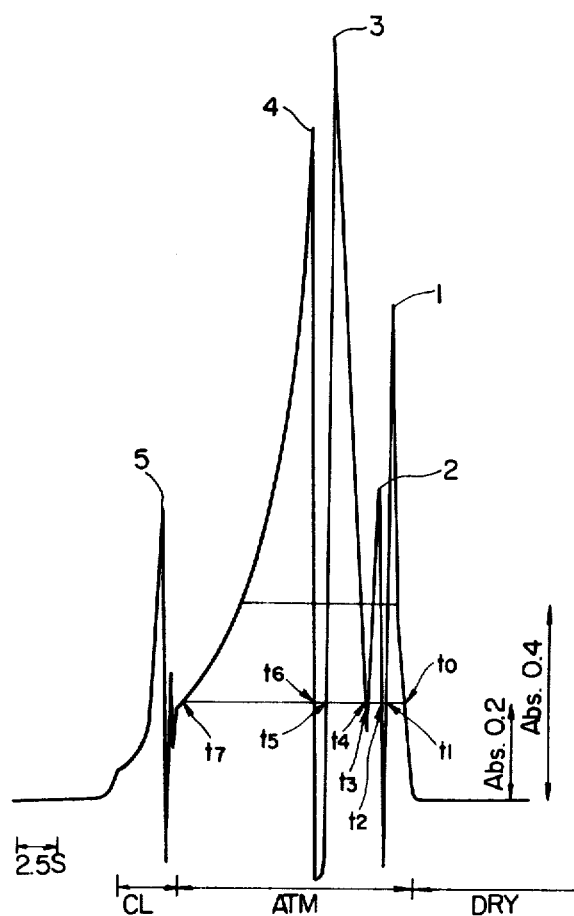
FIG. 3 is a graph explaining the principle of the present invention due to the difference absorption peak of a sample having a high concentration.

FIG. 3 shows an example of an absorption peak which is attained by measuring 20,000 ppb (or 20 ppm) of lead by the Zeeman atomic absorption. The measurement was conducted at 110° C. for 17.5 secs. for a drying operation (DRY); at 2000° C. for 15 secs. for an atomizing operation (ATM); and at 2400° C. for 3.75 secs. for a cleaning operation (CL). Since the sample contains no organic substance, a laying in ashes operation is omitted. In this case where the concentration is 100 times as high as the example shown in FIG. 2, it is apparent that the absorption peak is complicated. In the example being explained, four peaks which are numbered at 1 to 4 appear in an atomizing stage. Numeral 5 indicates the peak in the cleaning stage. If the highest peak 3 appears here, it is impossible to accomplish the quatitative analysis.

For the complex peaks thus far described, the present inventors studied the time periods at which the value of the absorption peak reaches a preset absorbance in the atomizing stage. In the example shown in FIG. 3, for instance, at the respective times $t_0$, $t_1$, $t_2$,–$t_7$ the absorbance (Abs) takes a value of 0.2 in the atomizing stage. Here, it was found that the difference ($t_7$–$t_0$) between the times $t_7$ and $t_0$ has a close relationship with the concentration of the sample.

One embodiment of the present invention will be described with reference to FIGS. 4 and 5. First of all, the Zeeman atomic absorption spectrophotometer diagrammatically shown in FIG. 4 will be explained. A light source 10 is turned on by the current which is supplied from a power source 12. The light emitted from the light source 10 enters a polarizing element 14. The light emanating from this polarizing element 14 is a linearly polarized light having a predetermined polarizing plane. Moreover, the polarizing element 14 is rotating so that the polarizing plane of the linearly polarized light is accordingly turned. The light emanating from the polarizing element 14 enters an atomizing unit 16 made of a graphite tube, where it is absorbed by atomic vapor. A magnetic field of 10 KG is impressed upon that atomizing unit 16 by the actions of a pair of magnets 18. As a result, the absorption line at the atomizing unit 16 is split by the Zeeman effect. The light having passed through the atomizing unit 16 enters a detector after the light having a preset wavelength has been selected by a monochrometer 20. An electric signal corresponding to the intensity of the incident light is generated by the detector 22. The electric signal thus generated is amplified by a preamplifier 24 and subjected to logarithmic conversion by a logarithmic converter 26. The signal thus converted is fed to a synchronous rectifier 30 after its noise component has been removed by a band-pass filter 28 having a center frequency $f_1$. From a gate circuit 32, on the other hand, there is fed to the synchronous rectifier 30 a gate signal having the frequency $f_1$ synchronized with the rotations of the polarizing element 14. As a result, the signal input into the synchronous rectifier 30 is rectified. The output signal from the synchronous rectifier 30 is indicative of such an absorbance as is varied with the time, as shown in FIG. 3. This signal is recorded in a recorder (Rec) and is also passed to a time measuring circuit 33.

Next, the construction and operation of a time measuring circuit 33 according to the embodiment of the present invention will be explained with reference to FIGS. 4 and 5. A temperature control unit 34 is provided in the time measuring circuit 33. This unit 34 is a logical control circuit for controlling the temperature of the atomizing unit 16 in accordance with known requirements for the atomizing operation and for generating signals as shown in FIG. 5 corresponding to the respective stages of the drying operation (DRY), the atomizing operation (ATM) and the cleaning operation (CL). The output absorption signal from the synchronous rectifier 30 is fed to one input of a comparator 36. The other input of the comparator 36 receives a reference voltage Vref from a reference power source 38. This reference voltage Vref is, for example, a voltage corresponding to the Abs 0.2 in FIG. 3. When the output from the synchronous rectifier 30 becomes coincident with the reference voltage Vref, the output COMP in generated in the comparator 36. This output COMP is applied to an AND gate 40. The other input of the AND gate 40 receives the signal ATM indicative of the atomizing stage from the temperature control unit 34. As a result, the AND gate 40 becomes conductive only in the atomizing stage. As shown in FIG. 3, when the absorbance first reaches 0.2 at the time $t_0$ in the atomizing stage (ATM), a pulse is generated by the AND gate 40. In response to this pulse, a flip-flop 42 is set so that a Q output is raised to a high level as shown in FIG. 5. And, an AND gate 44 becomes conductive so that the output pulse from an oscillator 46 is applied to the input UP of a counter 48, to start the counting operation. In other words, the counting operation is started at the time $t_0$ in FIG. 3. Here, for example, a pulse oscillator of 10 ms can be used as the oscillator 46, and a BCD counter of four figures can be used as the counter. Then, when a coincidence output pulse is generated at the time $t_1$ by the comparator 36, it is applied through the AND gate 40 to the load terminal L of a latch circuit 50. In response to the input pulse to the load terminal L, more specifically, the latch circuit 50 latches the counted value of the counter 48 at that time. As a result, there is held in the latch circuit 50 the time period from the time $t_0$ to the time $t_1$. At the time $t_2$, in response to the output from the AND gate 40, the latch circuit 50 latches the counted value of the counter 48 to that time, i.e., the time period ($t_2$–$t_0$). Thus, at the times $t_3$, $t_4$, –$t_7$, the respective times elapsing from the time $t_0$ are held in the latch circuit 50. When the atomizing stage is finished, the AND gate 40 becomes non-conductive. Therefore, even if the coincidence signal COMP is generated in the cleaning stage by the comparator 36 as shown by the last pulse on the line labelled COMP in FIG. 5, the latch circuit 50 will not carry out its latching operation at that time. In response to the output CL from the temperature control unit 34, which indicates the cleaning stage CL, on the other hand, the flip-flop 42 is reset so that the AND gate 44 becomes non-conductive. The content of the latch circuit 50 is indicated in a display unit 52. This display unit consists of, for example, a seven-segment decoder driver and a seven-segment display element. Incidentally, the counter 48 and the latch circuit 50 are cleared by the signal DRY coming from the temperature control unit 34, which indicates the drying stage DRY.

The optical system of the Zeeman atomic absorption spectrophotometer thus far described is an example in which a DC magnetic field is impressed upon the atomizing unit and in which the impressing direction intersects the optical axis. However, there are various systems known as the optical systems of the Zeeman atomic absorption spectrophotometer. For example, such various optical systems can be practiced by combining the impression of the magnetic field upon the light source, the modulation of the intensity of the magnetic field, and the arrangement of the impressing direction of the magnetic field in parallel with the optical axis. In accordance with those modifications, moreover, various cases can be conceived including the case in which the polarizing element is made rotatable or fixed or in which the polarizing element is arranged in front of the detector. The present embodiment is effective for any of the optical systems thus far described.

On the other hand, although the time measurement is performed only for a preset absorptivity, e.g., 0.2 in the foregoing description, the time may be measured for a plurality of absorptivities if desired. By way of an example of what is shown in FIG. 3, more specifically, the absorbance at the end of the atomizing stage is 0.19. As a result, in case the measurement is made for a preset absorbance of 0.1, it will lead to an erroneous measurement. For quantification of an unknown sample, therefore, it is preferable to conduct the time measurement by providing a plurality of stages of preset values. Moreover, although permeability may be used as the preset values, generally the preset values are the absorbance because an absorbance display is more commonly made in atomic absorption analysis. On the other hand, if the measurement involves a sample having a low concentration, it is also effective for the actual analysis that the quantification resorting to the absorption peak value is used together with the quantification based on the method of this invention.

Figure 6:
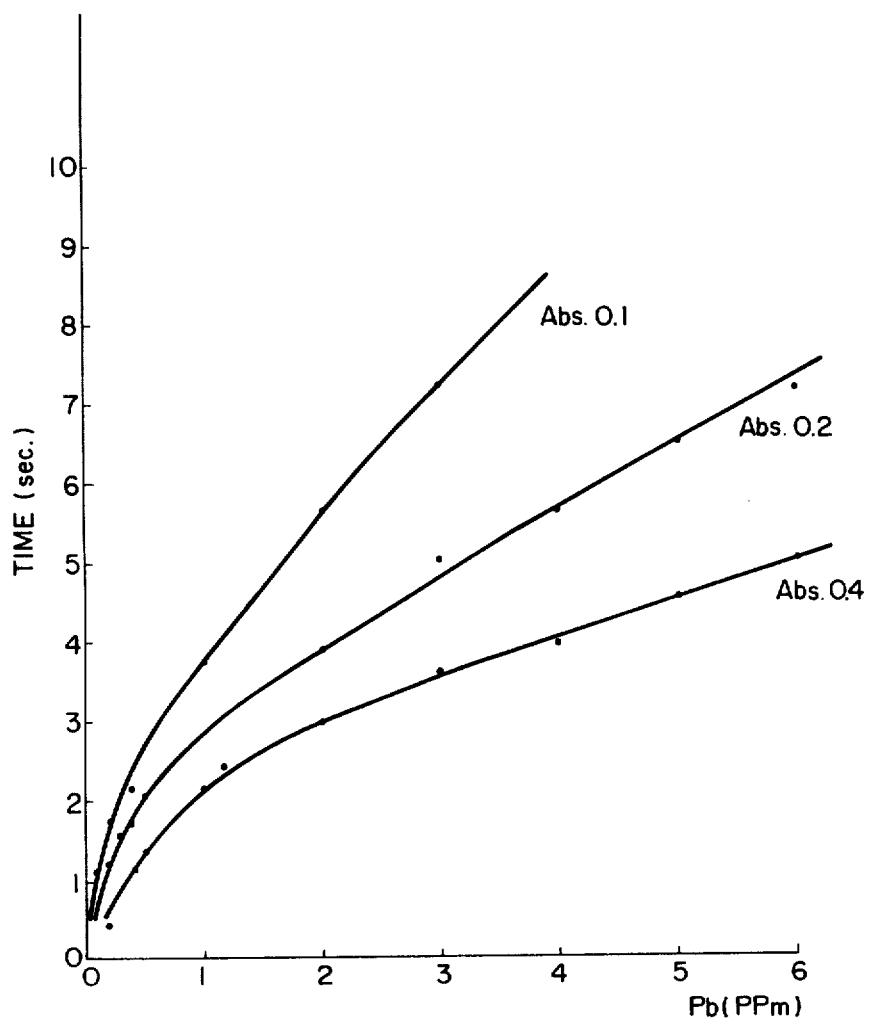
FIGS. 6 and 7 are charts of the calibrated curves which are obtained by the embodiment of the present invention.

In FIG. 6, the relationship between the concentrations and times are plotted by measuring the time periods in the manner described above for absorbance values Abs equal to 0.1, 0.2 and 0.4 as to samples having a plurality of concentrations from 0.1 ppm (or 100 ppb) to 6 ppm. The points, which are plotted for the respective absorbances, substantially lie on the respective preset curves. As a result, those curves can be used as standard calibration curves.

Figure 7:
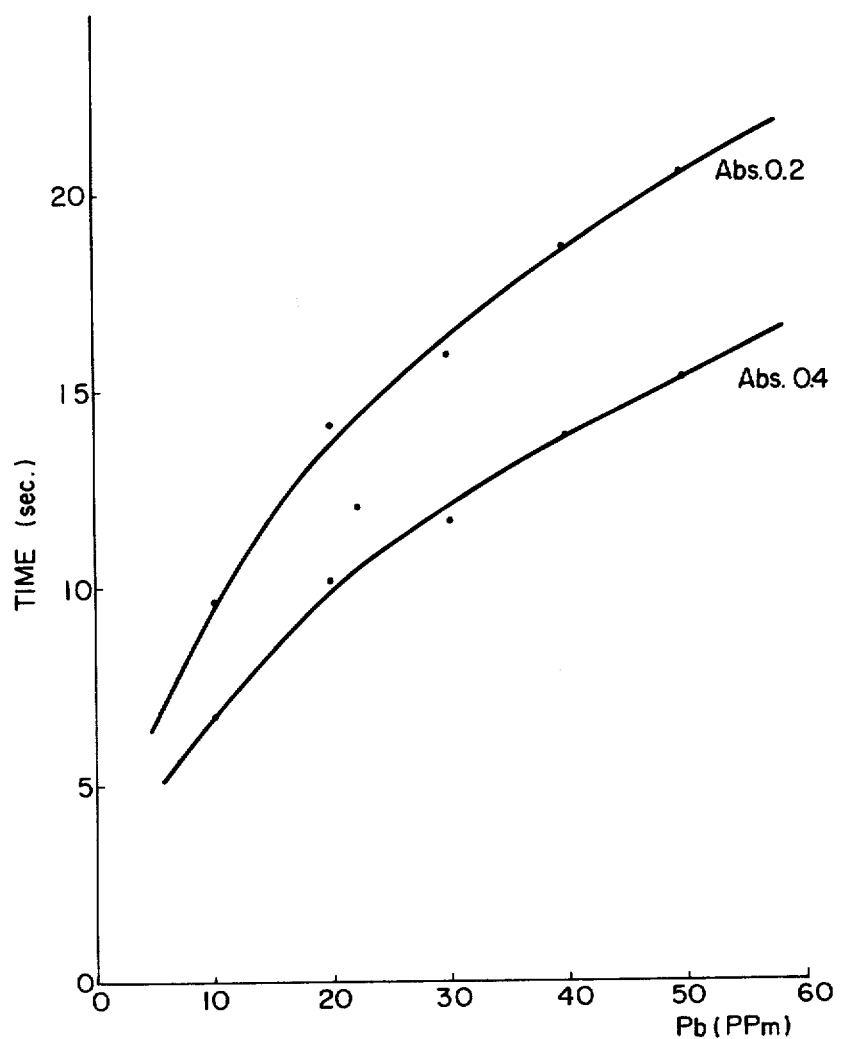

In FIG. 7, the relationship between the concentrations and times are plotted by measuring the time periods for absorbance values Abs of 0.2 and 0.4 as to samples having a plurality of concentrations from 1 ppm to 50 ppm.

For lead, it is apparent from FIGS. 6 and 7 that the draw-back phenomenon does not appear up to the high concentration of 60 ppm. Taking it into consideration that the draw-back phenomenon of the calibration curve appears from about 1 ppm upon the analysis of lead by the conventional Zeeman atomic absorption method, it is apparent that the present invention is effective for the measurement of the sample having a high concentration.

According to the results of experiments using lead, the measurements can be performed up to 100 ppm. This means that the concentration limit of 1 ppm up to which measurement can be performed by the conventional method has been increased 100 times. Moreover, it has also been ascertained in experiments using cadmium that a concentration at which the measurement can be performed can also be increased 100 times.

Thus, according to the embodiment of the present invention discussed up to this point, a sample having a higher concentration than the conventional one can be analyzed.

Another embodiment of the present invention will be described with reference to FIG. 8. Reference numerals which are the same as those appearing in FIG. 4 indicate similar parts.

Figure 4:
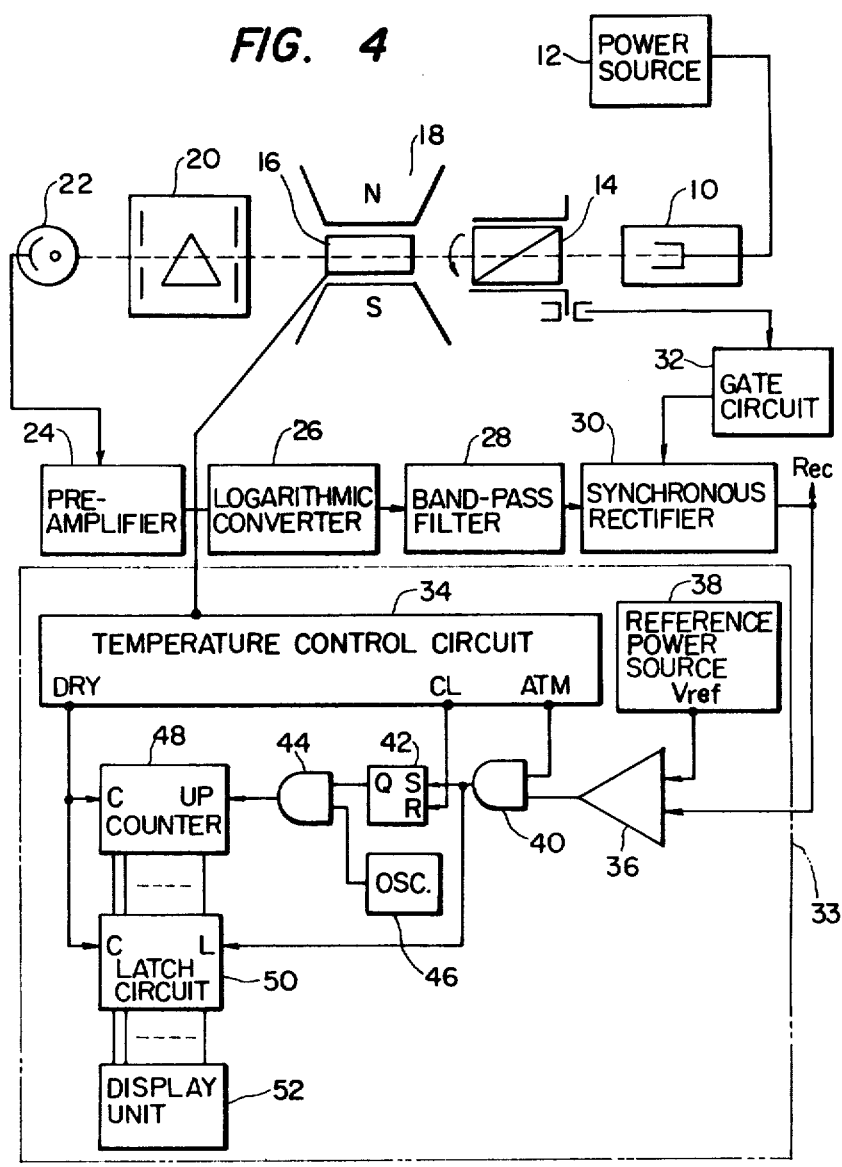
FIG. 4 is a block diagram of one embodiment of the present invention.
Figure 5:
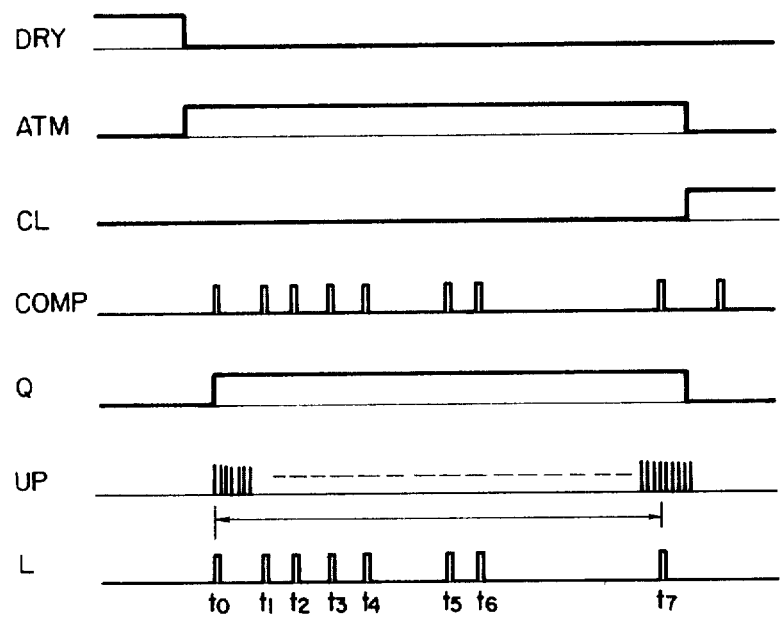
FIG. 5 is a time chart for the embodiment shown in FIG. 4.
Figure 8:
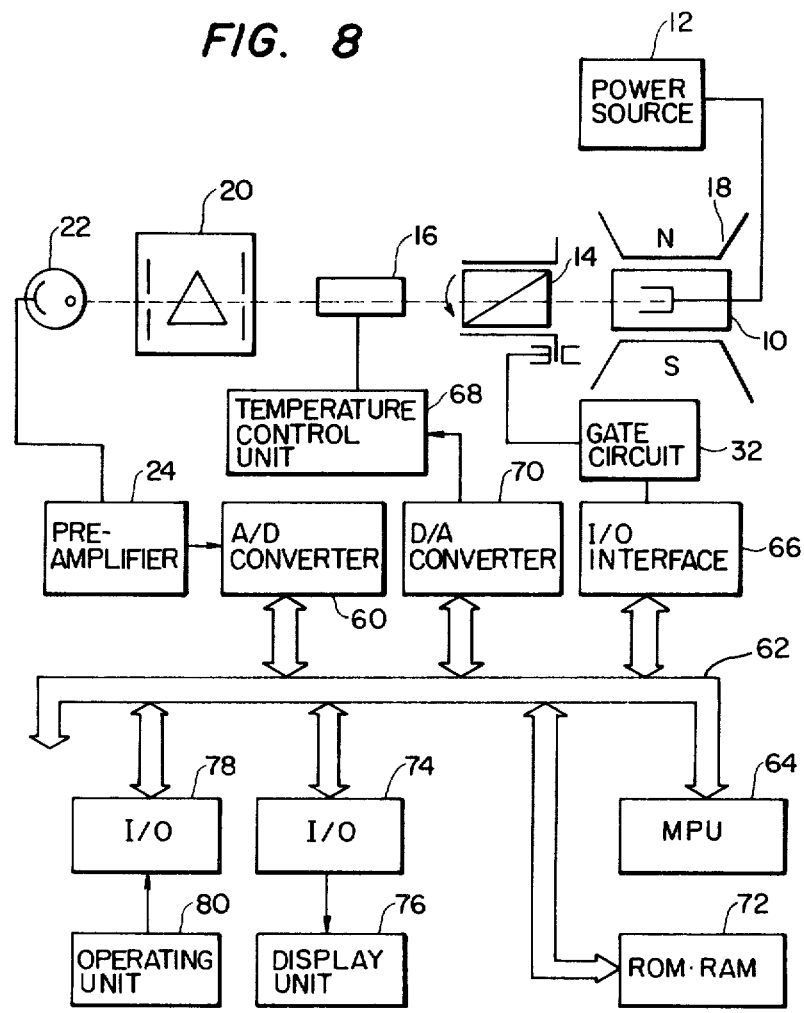
FIG. 8 is a block diagram of another embodiment of the present invention.

The difference in the optical system of this embodiment of FIG. 8 from the embodiment shown in FIG. 4 resides in that the magnetic field by the magnets 18 is impressed not upon the atomizing unit 16 but upon the light source 10. As a result, the beam emanating from the light source 10 is split by the Zeeman effect. And, components $\pi$ and $\rho\pm$ are separated by the action of the polarizing element 14 in accordance with the difference between their polarizing planes.

The difference in the signal processing system of FIG. 8 from that of FIG. 4 resides in that a microprocessor unit (MPU) is used. The output from the detector 22 is amplified by the pre-amplifier 24 and is converted into a digital signal by the action of an A/D converter 60. The digital signal thus converted is applied through a bus line 62 to an MPU 64. On the other hand, the gate signal from the gate circuit 32 is applied through an input/output interface I/O 66 to the MPU 64. The atomizing unit 16 has its temperature control unit 68 controlled through a D/A converter 70 by the MPU 64.

Figure 9:
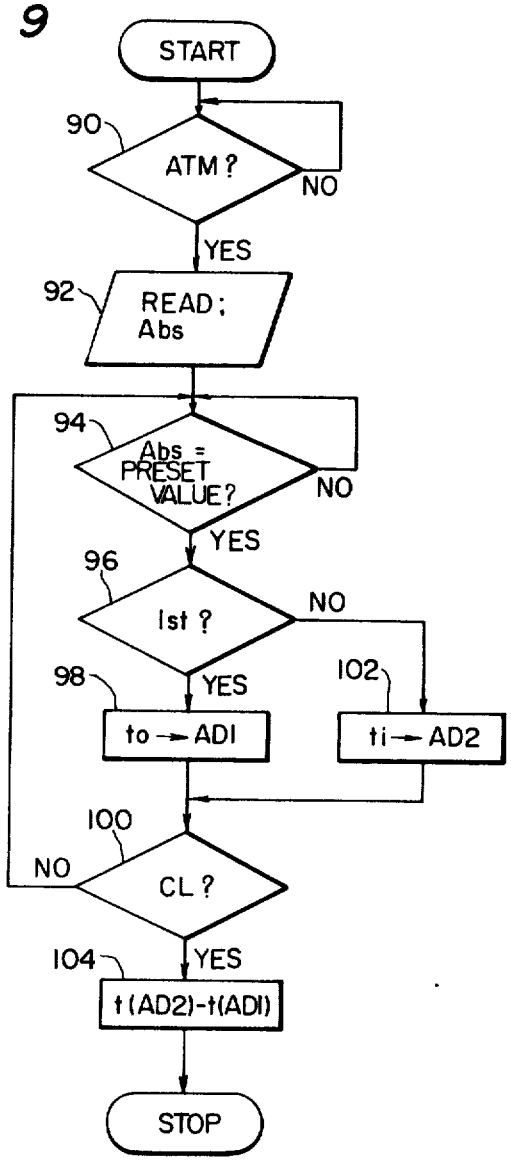
FIG. 9 is a flow chart of the embodiment shown in FIG. 8.

The program for measuring the time period during the atomizing stage from the time when the absorbance first reaches a preset value to the time when the same reaches the preset value for the last time during the atomizing stage is memorized in advance in a ROM 72. This program will be explained with reference to the flow chart shown in FIG. 9. At a judgment 90, it is determined whether or not the measurement is in the atomizing stage ATM so that the program advances to the next step if it is in the atomizing stage. The data Abs of absorbance is consecutively read in an input 92. Whether or not the data Abs read is of preset values such as 0.2 or 0.4 or not is judged at a judgment step 94. When the data Abs read reaches a preset value, whether or not it is the first time this value is reached is judged at a judgment step 96. When it is the first time, the time $t_0$ at that instant is memorized at a processing step 98 in the first address AD1 of the RAM 72. In the atomizing stage, moreover, "NO" is judged at a judgment step 100. Thus, the loop from the judgment step 94 to the judgment step 100 is repeated. And, when the data Abs is read after the second time the measurement reaches a preset value, it is advanced at the judgment step 96 to a processing step 102. In other words, the time $t_i$ when the read data Abs reach the preset value is memorized in a second address AD2. And, the content of the address AD2 is changed one after another in the atomizing stage. If the above is judged in the cleaning stage CL at the judgment step 100, the difference between the time memorized in the address AD2 and the time memorized in the address AD1 is operated on at a processing step 104. The operational results are indicated through an I/O 74 in a display unit 76.

Although the magnetic field is impressed upon the light source in the foregoing description, the present invention can be applied to various types of Zeeman atomic absorption photometers, as has been described before.

Moreover, although it has also been described that the preset value of absorptivity is memorized in advance in the ROM 72, that preset value may be fed from an operating unit 80 through an I/O 78. On the other hand, a plurality of preset values can be provided as discussed previously with respect to FIG. 4.

On the other hand, although the calibration curves shown in FIGS. 6 and 7 have curvatures, calibration curves having excellent linearities can be obtained by determining the values of $f(t_n-t_0)$ having a linear relationship with the concentration. In the examples shown in FIGS. 6 and 7, excellent linearities can be obtained by performing the calculations while assuming the function f as a quadratic equation. This can be accomplished by preparing samples having known different concentrations, by feeding the concentration values in advance from the operating unit 80, by measuring the time periods as to the preset absorbance and by accomplishing the quadratic function approximation on the basis of the measured values for the respective concentrations.

In summary, in accordance with the present invention as described herein, it is possible to accomplish analysis of samples in a higher concentration than in prior art with the use of the Zeeman atomic absorption spectrophotometer.

It is to be understood that the above-described arrangements are simply illustrative of the application of the principles of this invention. Numerous other arrangements may be readily devised by those skilled in the art which embody the principles of the invention and fall within its spirit and scope.

We claim:

1. A Zeeman atomic absorption spectrophotometer comprising:
a light source;
an atomization section irradiated with the light from said light source including means for atomizing a sample;
a detector coupled to receive the light emitted from said light source and then subjected to atomic absorption in said atomization section, and to convert the light into an electric signal;
means for generating a pair of Zeeman split light components emitted from the light source including means for applying a magnetic field to the light source;
means coupled to the output of said detector for processing the detected signal and producing an atomic absorption signal for the sample, which signal is corrected for background absorption; and
means for measuring, during a stage of atomization of the sample in said atomization section, the length of time between an instant at which the intensity of the background absorption-corrected atomic absorption signal initially reaches a predetermined level and an instant at which the intensity of the same signal reaches the same predetermined level for the last time during said stage of atomization.

2. A Zeeman absorption spectrophotometer according to claim 1, wherein said time measuring means comprises a reference signal source for generating an output of a predetermined level, means for comparing the atomic absorption signal with the reference signal, and a time counter actuated with an output from said comparing means.

3. A Zeeman atomic absorption spectrophotometer according to claim 1, wherein said time measuring means includes a means for controlling the temperature of said atomization section, said temperature controlling means producing an output signal indicating that the atomization of sample is being carried out.

4. A Zeeman atomic absorption spectrophotometer according to claim 1, wherein said time measuring means comprises a microprocessor, a random access memory and a read-only memory, said read-only memory memorizing a program comprising a step of successively reading atomic absorption signals during the atomization of the sample, a step of ascertaining that an atomic absorption signal is as high as a predetermined level, a step of successively memorizing an instant at which an atomic absorption signal is as high as a predetermined level, and a step of operating the length of time between an instant at which an atomic absorption signal initially reaches a predetermined level and an instant at which the same signal reaches the same predetermined level for the last time during the atomization stage, said microprocessor being adapted to carry out an operation in accordance with the program by utilizing a memory area in said random access memory.

5. A Zeeman atomic absorption spectrophotometer according to claim 2, 3 or 4, wherein a plurality of predetermined levels is preset.

6. A Zeeman atomic absorption spectrophotometer according to claim 2, 3 or 4, wherein the direction in which a magnetic field is applied from said magnetic field applying means is at right angles to an optical axis of the path of said light.

7. A Zeeman atomic absorption spectrophotometer according to claim 6, wherein the intensity of the magnetic field generated by said magnetic field applying means is constant.

8. A Zeeman atomic absorption spectrophotometer according to claim 2, 3 or 4, wherein the direction in which a magnetic field is applied from said magnetic field applying means is parallel to the optical axis of the path of said light.

9. A Zeeman atomic absorption spectrophotometer according to claim 8, wherein the intensity of magnetic field generated by said magnetic field applying means is constant.

10. A Zeeman atomic absorption spectrophotometer according to claim 1, further comprising a rotating polarizer coupled between the light source and the detector.

11. A Zeeman atomic absorption spectrophotometer according to claim 1, wherein the time measuring means comprises a reference signal source for generating an output of a predetermined level, means for comparing the atomic absorption signal with the reference signal, and a time counter actuated with an output from said comparing means, and further includes means responsive to the indication signal from the temperature control means for only passing the output of the comparing means to said time counter when the atomization indication signal is present.

12. A Zeeman atomic absorption spectrophotometer comprising:
means for positioning an atomized unknown sample on an optical axis;
means positioned along the optical axis to pass light from a light source of a predetermined wavelength through atomic vapors of said atomized sample;
means for generating Zeeman split light components emitted from the light source including means for applying a magnetic field to said light source;
means for detecting the Zeeman split light components which have passed through the atomic vapors to provide an atomic absorption signal; and means for successively detecting instants $t_0, t_1 \ldots t_n$ at which a detected atomic absorption signal attains a predetermined level and for determining the difference between $t_n$ and $t_0$.

13. A Zeeman atomic absorption spectrophotometer according to claim 12, wherein said difference determining mechanism comprises means for comparing the atomic absorption signals with a predetermined value, and a time measuring means actuated by an output from said comparing means.

14. A Zeeman atomic absorption spectrophotometer according to claim 13, wherein said time measuring means comprises a counter adapted to start a counting operation at instant $t_0$, and a latch circuit adapted to latch the content of said counter at the instants $t_1, t_2 \ldots t_n$.

15. A Zeeman atomic absorption spectrophotometer according to claim 12, wherein said difference determining means comprises a microprocessor, a random access memory, and a read-only memory, said microprocessor operating to fetch atomic absorption signals successively, to judge the atomic absorption signals successively at instants $t_0, t_1 \ldots t_n$, to memorize the instants $t_0, t_1 \ldots t_n$ successively in said random access memory, and thereafter to determine the difference between the instants $t_n$ and $t_0$.

16. A Zeeman atomic absorption spectrophotometer according to claim 15, wherein said random access memory has two memory areas; and said microprocessor operates to memorize the instant $t_0$ in a first memory area and renew the content of a second memory area at each of the instants $t_1, t_2 \ldots t_n$.

17. A Zeeman atomic absorption spectrophotometer according to claim 13 or 15, wherein a plurality of predetermined levels are preset.

18. A Zeeman atomic absorption spectrophotometer according to claim 13 or 15, wherein the direction in which a magnetic field is applied from said magnetic field applying means is at right angles to the optical axis.

19. A Zeeman atomic absorption spectrophotometer according to claim 13 or 15, wherein the direction in which a magnetic field is applied from said magnetic field applying means is parallel to the optical axis.

20. A Zeeman atomic absorption spectrophotometer according to claim 13 or 15, wherein the intensity of magnetic field of said magnetic field applying means is constant.

21. A Zeeman atomic absorption spectrophotometer comprising:

a light source;

an atomization section irradiated with the light from said light souree including means for atomizing a sample;

a detector coupled to receive the light emitted from said light source and then subjected to atomic absorption in said atomization section, and to convert the light into an electric signal;

means for generating a pair of Zeeman split components produced in the atomization section including means for applying a magnetic field to the atomization section;

means coupled to the output of said detector for processing the detected signal and producing an atomic absorption signal for the sample, which signal is corrected for background absorption; and means for measuring, during a stage of atomization of the sample in said atomization section, the length of time between an instant at which the intensity of the background absorption-corrected atomic absorption signal initially reaches a predetermined level and an instant at which the intensity of the same signal reaches the same predetermined level for the last time during said stage of atomization.

22. A Zeeman atomic absorption spectrophotometer according to claim 21, wherein said time measuring means comprises a reference signal source for generating an output of a predetermined level, means for comparing the atomic absorption signal with the reference signal, and a time counter actuated with an output from said comparing means.

23. A Zeeman atomic absorption spectrophotometer according to claim 21, wherein said time measuring means include a means for controlling the temperature of said atomization section, said temperature controlling means producing an output signal indicating that the atomization of sample is being carried out.

24. A Zeeman atomic absorption spectrophotometer according to claim 21, wherein said time measuring means comprises a microprocessor, a random access memory and a read-only memory, said read-only memory memorizing a program comprising a step of successively reading atomic absorption signals during the atomization of the sample, a step of ascertaining that an atomic absorption signal is as high as a predetermined level, a step of successively memorizing an instant at which an atomic absorption signal is as high as a predetermined level, and a step of operating the length of time between an instant at which an atomic absorption signal initially reaches a predetermined level and an instant at which the same signal reaches the same predetermined level for the last time during the atomization stage, said microprocessor being adapted to carry out an operation in accordance with the program by utilizing a memory area in said random access memory.

25. A Zeeman atomic absorption spectrophotometer according to claim 22, 23 or 24, wherein a plurality of predetermined levels is preset.

26. A Zeeman atomic absorption spectrophotometer according to claim 22, 23 or 24, wherein the direction in which a magnetic field is applied from said magnetic field applying means is at right angles to an optical axis of the path of said light.

27. A Zeeman atomic absorption spectrophotometer according to claim 26, wherein the intensity of the magnetic field generated by said magnetic field applying means is constant.

28. A Zeeman atomic absorption spectrophotometer according to claim 22, 23 or 24, wherein the direction in which a magnetic field is applied from said magnetic field applying means is parallel to the optical axis of the path of said light.

29. A Zeeman atomic absorption spectrophotometer according to claim 28, wherein the intensity of magnetic field generated by said magnetic field applying means is constant.

30. A Zeeman atomic absorption spectrophotometer according to claim 21, further comprising a rotating polarizer coupled between the light source and the detector.

31. A Zeeman atomic absorption spectrophotometer according to claim 21, wherein the time measuring means comprises a reference signal source for generating an output of a predetermined level, means for comparing the atomic absorption signal with the reference signal, and a time counter actuated with an output from said comparing means, and further includes means responsive to the indication signal from the temperature control means for only passing the output of the comparing means to said time counter when the atomization indication signal is present.

32. A Zeeman atomic absorption spectrophotometer comprising:
means for positioning an atomized unknown sample on an optical axis;
means positioned along the optical axis to pass light of a predetermined wavelength through atomic vapors of said atomized sample;
means for generating Zeeman split light components produced in the atomized sample including means for applying a magnetic field to said atomized sample;
means for detecting the light which has passed through the atomic vapors to provide an atomic absorption signal; and
means for successively detecting instants $t_0, t_1 \ldots t_n$ at which a detected atomic absorption signal attains a predetermined level and for determining the difference between $t_n$ and $t_0$.

33. A Zeeman atomic absorption spectrophotometer according to claim 32, wherein said difference determining mechanism comprises means for comparing the atomic absorption signals with a predetermined value, and a time measuring means actuated by an output from said comparing means.

34. A Zeeman atomic absorption spectrophotometer according to claim 33, wherein said time measuring means comprises a counter adapted to start a counting operation at instant $t_0$, and a latch circuit adapted to latch the content of said counter at the instants $t_1, t_2 \ldots t_n$.

35. A Zeeman atomic absorption spectrophotometer according to claim 32, wherein said difference determining means comprises a microprocessor, a random access memory, and a read-only memory, said microprocessor operating to fetch atomic absorption signals successively, to judge the atomic absorption signals successively at instants $t_0, t_1 \ldots t_n$, to memorize the instants $t_0, t_1 \ldots t_n$ successively in said random access memory, and thereafter to determine the difference between the instants $t_n$ and $t_0$.

36. A Zeeman atomic absorption spectrophotometer according to claim 35, wherein said random access memory has two memory areas; and said microprocessor operates to memorize the instant $t_0$ in a first memory area and renew the content of a second memory area at each of the instants $t_1, t_2 \ldots t_n$.

37. A Zeeman atomic absorption spectrophotometer according to claim 33 or 35, wherein a plurality of predetermined levels are preset.

38. A Zeeman atomic absorption spectrophotometer according to claim 33 or 35, wherein the direction in which a magnetic field is applied from said magnetic field applying means is at right angles to the optical axis.

39. A Zeeman atomic absorption spectrophotometer according to claim 33 or 35, wherein the direction in which a magnetic field is applied from said magnetic field applying means is parallel to the optical axis.

40. A Zeeman atomic absorption spectrophotometer according to claim 33 or 35, wherein the intensity of magnetic field of said magnetic field applying means is constant.

* * * * *